US007569015B2

(12) United States Patent
Donaldson et al.

(10) Patent No.: US 7,569,015 B2
(45) Date of Patent: Aug. 4, 2009

(54) INTEGRATED PHYSIOLOGY AND IMAGING WORKSTATION (75) Inventors: Brenda Donaldson, Harrison Township, MI (US); Israel Raz, Highland Park, IL (US); Sachin Vadodaria, Fox Point, WI (US)

(73) Assignee: General Electric Company, Schenectady, NY (US)

( * ) Notice: Subject to any disclaimer, the term of this patent is extended or adjusted under 35 U.S.C. 154(b) by 561 days.

(21) Appl. No.: 11/182,473

(22) Filed: Jul. 15, 2005

(65) Prior Publication Data

US 2007/0016028 A1    Jan. 18, 2007

(51) Int. Cl.
A61B 8/00    (2006.01)
A61B 5/0402    (2006.01)

(52) U.S. Cl. .......................... 600/437; 600/523

(58) Field of Classification Search ............... 600/407, 600/410, 411, 437, 440–443, 453–457, 476–480, 600/509, 523
See application file for complete search history.

(56) References Cited

U.S. PATENT DOCUMENTS

| 5,203,337 | A | | 4/1993 | Feldman |
| 5,391,199 | A | | 2/1995 | Ben-Haim |
| 5,409,000 | A | | 4/1995 | Imran |
| 5,432,544 | A | * | 7/1995 | Ziarati ........................ 600/410 |
| 5,438,997 | A | | 8/1995 | Sieben et al. |
| 5,568,809 | A | | 10/1996 | Ben-Haim |
| 5,579,764 | A | | 12/1996 | Goldreyer |
| 5,588,432 | A | | 12/1996 | Crowley |
| 5,662,108 | A | | 9/1997 | Budd et al. |
| 5,687,737 | A | | 11/1997 | Branham et al. |
| 5,713,946 | A | | 2/1998 | Ben-Haim |
| 5,771,895 | A | | 6/1998 | Slager |
| 5,840,031 | A | * | 11/1998 | Crowley .................... 600/440 |
| 6,019,725 | A | | 2/2000 | Vesely et al. |
| 6,086,532 | A | | 7/2000 | Panescu et al. |
| 6,102,863 | A | * | 8/2000 | Pflugrath et al. ............ 600/447 |
| 6,168,565 | B1 | | 1/2001 | Napolitano |
| 6,200,269 | B1 | | 3/2001 | Lin et al. |
| 6,216,027 | B1 | | 4/2001 | Willis et al. |
| 6,246,898 | B1 | | 6/2001 | Vesely et al. |
| 6,325,759 | B1 | | 12/2001 | Pelissier |
| 6,389,311 | B1 | * | 5/2002 | Whayne et al. ............. 600/523 |

(Continued)

FOREIGN PATENT DOCUMENTS

DE    103 40 546 A1    3/2005

(Continued)

*Primary Examiner*—Eric F Winakur
(74) *Attorney, Agent, or Firm*—Dean Small; The Small Patent Law Group (57) ABSTRACT A physiology workstation is provided that comprises a communications interface conveying physiology signals derived from a subject and ultrasound data representative of a region of interest of the subject. The ultrasound data is obtained by an ultrasound device in real-time during a procedure carried out on the subject. An physiology processing unit receives and processes the physiology signals. An ultrasound processing unit receives and processes the ultrasound data to generate ultrasound images. The physiology processing unit combines the physiology signals with the ultrasound images from the ultrasound processing unit. A display unit displaying the physiology signals and the ultrasound images. The physiology signals and ultrasound signals are presented jointly to a user in real-time during the procedure being carried out on the subject.

30 Claims, 8 Drawing Sheets

U.S. PATENT DOCUMENTS

| | | |
|---|---|---|
| 6,413,219 B1 | 7/2002 | Avila et al. |
| 6,447,450 B1 | 9/2002 | Olstad |
| 6,505,063 B2 | 1/2003 | Van Den Brink et al. |
| 6,537,217 B1 | 3/2003 | Bjaerum et al. |
| 6,575,901 B2 | 6/2003 | Stoycos et al. |
| 6,650,927 B1 | 11/2003 | Keidar |
| 6,679,847 B1 | 1/2004 | Robinson et al. |
| 6,705,992 B2 * | 3/2004 | Gatzke ............... 600/437 |
| 6,728,562 B1 | 4/2004 | Budd et al. |
| 6,950,689 B1 | 9/2005 | Willis et al. |
| 7,263,397 B2 | 8/2007 | Hauck et al. |
| 7,285,117 B2 | 10/2007 | Krueger et al. |
| 7,314,446 B2 * | 1/2008 | Byrd et al. ............ 600/443 |
| 7,485,115 B2 | 2/2009 | Nakamura |
| 2003/0045795 A1 | 3/2003 | Bjaerum et al. |
| 2003/0074011 A1 | 4/2003 | Gilboa et al. |
| 2003/0120318 A1 | 6/2003 | Hauck |
| 2003/0163045 A1 | 8/2003 | Gatzke |
| 2003/0176778 A1 | 9/2003 | Messing et al. |
| 2004/0097806 A1 | 5/2004 | Hunter et al. |
| 2004/0080336 A1 | 7/2004 | Dala-Krishna et al. |
| 2004/0147842 A1 * | 7/2004 | Desmarais ............ 600/450 |
| 2004/0152974 A1 | 8/2004 | Solomon |
| 2004/0249259 A1 * | 12/2004 | Heimdal et al. ........ 600/407 |
| 2005/0013473 A1 | 4/2005 | Byrd et al. |
| 2005/0080336 A1 | 4/2005 | Byrd et al. |
| 2005/0090745 A1 * | 4/2005 | Steen .................. 600/447 |
| 2005/0096543 A1 | 5/2005 | Jackson et al. |
| 2005/0127798 A1 | 6/2005 | Arent et al. |
| 2005/0171428 A1 * | 8/2005 | Fichtinger et al. ...... 600/426 |
| 2005/0203375 A1 | 9/2005 | Willis et al. |
| 2006/0182320 A1 | 8/2006 | Peszynski et al. |
| 2006/0184016 A1 | 8/2006 | Glossop |
| 2006/0229594 A1 | 10/2006 | Francischelli et al. |
| 2006/0253030 A1 | 11/2006 | Altmann et al. |
| 2006/0253031 A1 | 11/2006 | Altmann et al. |
| 2006/0253032 A1 | 11/2006 | Altmann et al. |
| 2007/0130287 A1 | 6/2007 | Kumar et al. |
| 2007/0287902 A1 | 12/2007 | Fuimaono et al. |
| 2008/0177994 A1 | 7/2008 | Mayer |

FOREIGN PATENT DOCUMENTS

| | | |
|---|---|---|
| EP | 1 637 070 A | 3/2005 |
| WO | WO 92/19157 | 11/1992 |
| WO | WO 01/20552 A1 | 3/2001 |

* cited by examiner

INTEGRATED PHYSIOLOGY AND IMAGING WORKSTATION

BACKGROUND OF THE INVENTION

Embodiments of the present invention generally relate to physiology and imaging workstations, and more particularly to integrating various physiology and imaging features and functionality into a single workstation.

Today, physiology workstations are used in catheter labs, hemodynamic (HD) labs and electrophysiology (EP) labs to conduct various tests and procedures. Sometimes, the laboratory is organized into a procedure room, a control room and a remote monitoring room. Alternatively, there may not be a separate control or remote monitoring room. Instead, a sterile area where the patient lies is in the center of the room, and located in another area of the same room are the EP system and HP system, stimulator, etc. When available, the control and remote monitoring rooms are isolated from the sterile environment of the procedure room and are shielded from the x-rays generated in the procedure room by certain types of imaging equipment, such as fluoroscopy or CT imaging equipment. Presently, physiology workstations located in either the procedure, control or monitoring rooms are attached through cables to sensors, catheters, and instruments related only to the study. For example, conventional workstations are directly attached to surface ECG leads, intercardiac leads provided on a catheter, pressure sensors provided on a catheter and the like. The workstation is also directly attached to a stimulator that induces stimulus signals through a pacing tip on the catheter, such as to induce pacing to the heart.

Presently, the physiology workstation operates entirely separate and independent from imaging systems provided, such as an ultrasound workstation. The ultrasound workstation is a stand-alone system positioned in the procedure room proximate the patient and is controlled and operated by the physician or designated operator. The ultrasound system is attached to an ultrasound catheter or a surface probe that obtains ultrasound images. The ultrasound system is directly attached to a second set of surface ECG leads, separated and distinct from the surface ECG leads connected to the EP workstation. The ultrasound images are displayed on a dedicated ultrasound monitor positioned directly on the stand-alone ultrasound system in the procedure room. The ultrasound monitor in the procedure room is separate and distinct from the monitors in the control and remote monitoring rooms. The ultrasound system has a separate user interface dedicated and specific to ultrasound features and functionality. The ultrasound system also includes entirely independent and dedicated processing hardware and software, memory and the like. Thus, today, EP studies are performed utilizing a stand-alone ultrasound system that is separate and distinct from the electrophysiology workstation.

Conventional EP workstations and ultrasound systems suffer from various disadvantage, that are addressed by various embodiments of the present invention.

BRIEF SUMMARY OF THE INVENTION

A physiology workstation is provided that comprises a communications interface conveying physiology signals derived from a subject and ultrasound data representative of a region of interest of the subject. The ultrasound data is obtained by an ultrasound device in real-time during a procedure carried out on the subject. A processing unit receives and processes the physiology signals. An ultrasound processing unit receives and processes the ultrasound data to generate ultrasound images. The processing unit combines the physiology signals with the ultrasound images from the ultrasound processing unit. A display unit displaying the physiology signals and the ultrasound images. The physiology signals and ultrasound signals are presented jointly to a user in real-time during the procedure being carried out on the subject.

DETAILED DESCRIPTION OF THE INVENTION

Figure 1:
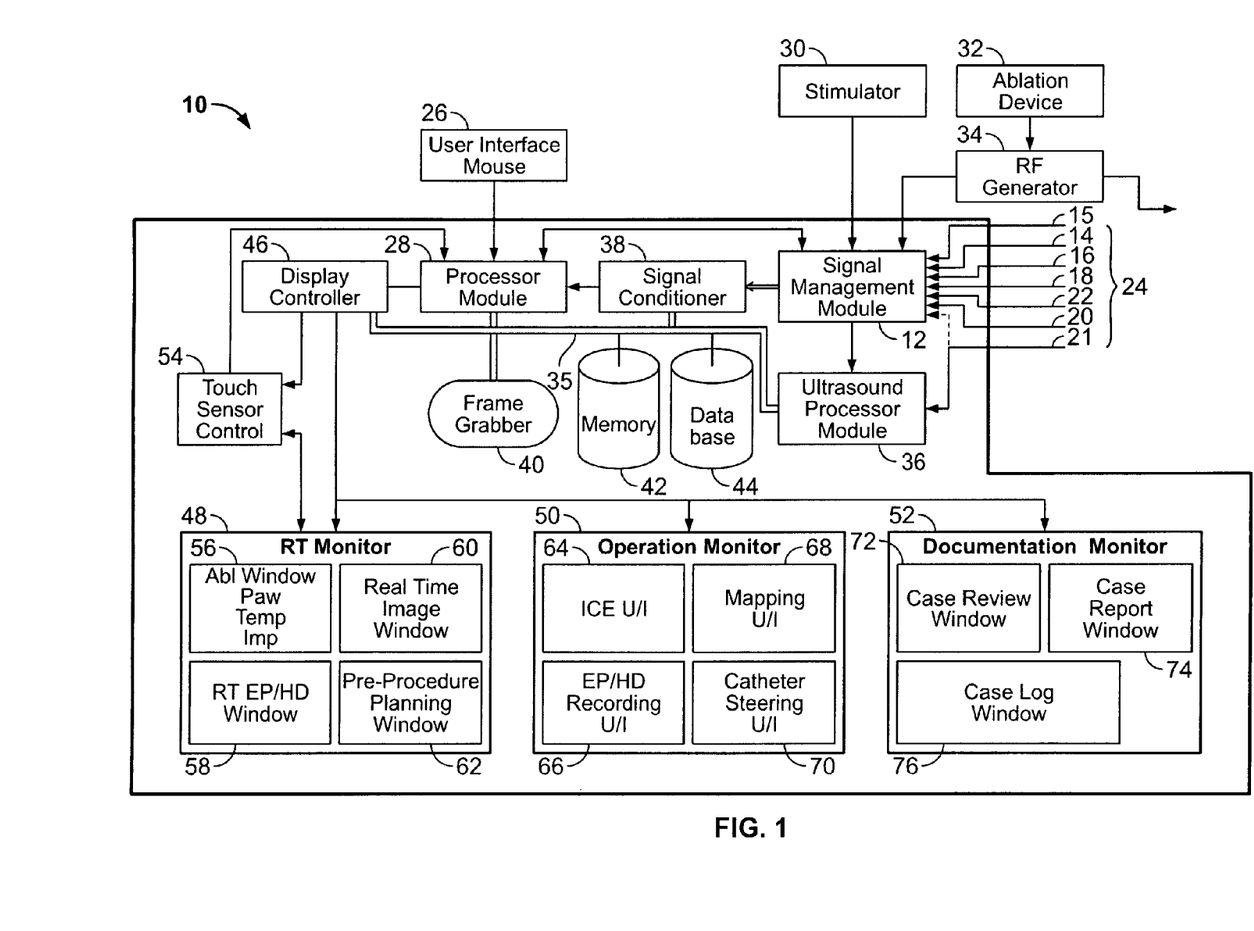
FIG. 1 illustrates a block diagram of a physiology workstation formed in accordance with an embodiment of the present invention.
Figure 2:
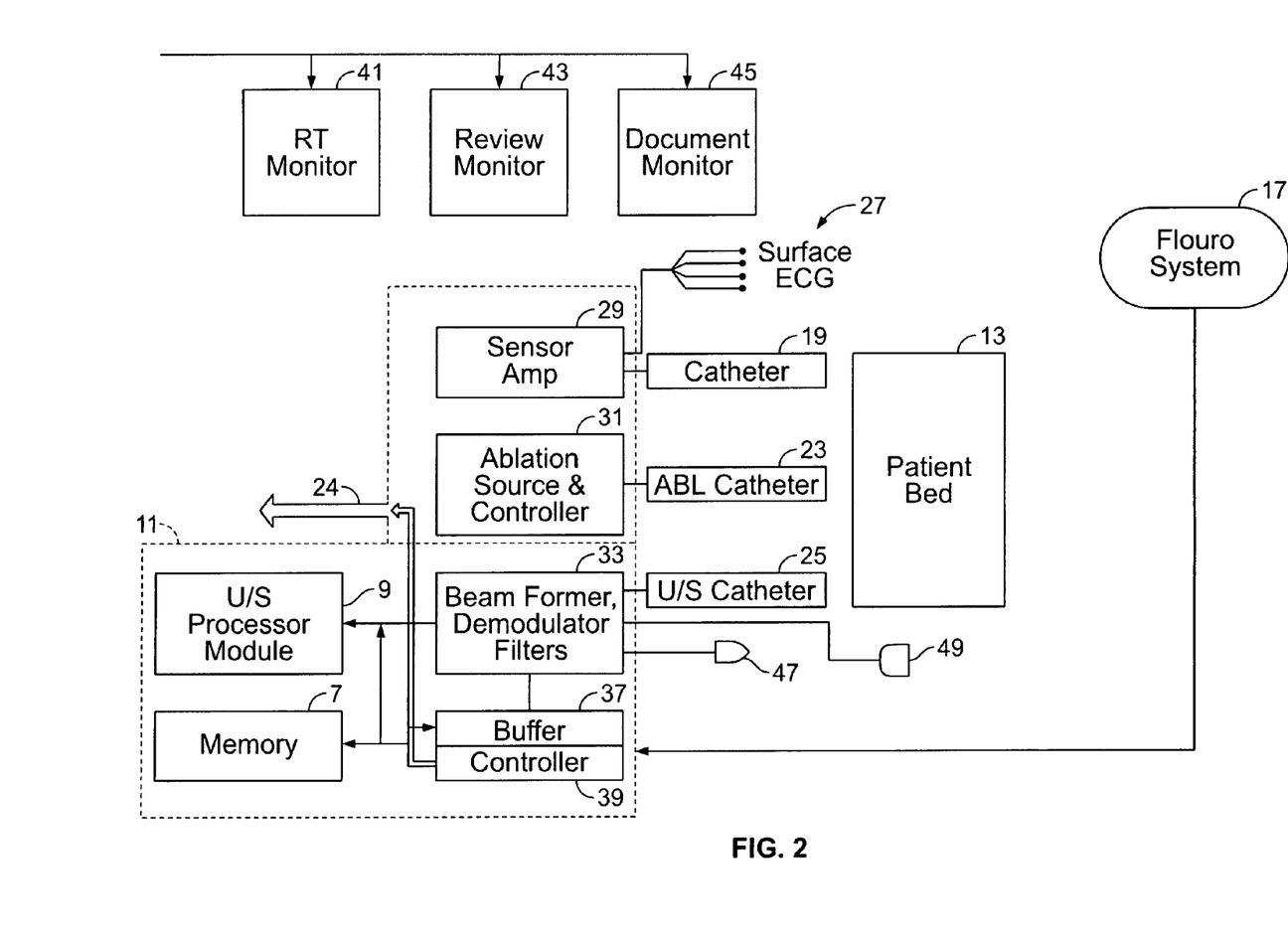
FIG. 2 illustrates a block diagram of ablation and imaging equipment in accordance with an embodiment of the present invention.

FIG. 1 illustrates a physiology workstation 10 formed in accordance with an embodiment of the present invention. The workstation 10 is located in a control room or procedural room and is utilized in connection with HD, EP and ablation procedures, among other things. FIG. 2 illustrates a procedure room which may be separate and discrete from the control room (when used) and from a remote monitoring room within the facility (e.g. a hospital, clinic and the like). The workstation 10 is operated by an operator, while the patient and procedure team are located in the procedure room. The workstation 10 integrates, among other things, real-time information, real-time intracardiac echography, fluoroscopic images, mapping data and pre-surgery planning CT & MR images. The workstation 10 offers integrated monitoring and review of HD, EP, patient, and mapping information as well as stored and real-time diagnostic images, ECG signals and IC signals.

As shown in FIG. 2, the procedure room includes an ultrasound system 11, a fluoroscopy system 17 and a patient bed 13 to hold the patient while an HD, EP or ablation procedure is carried out. The fluoroscopy system 17 is provided proximate patient bed 13 to obtain fluoroscopic images of the region of interest while the doctor is conducting a procedure. Catheters 19 (EP or HD), an ablation catheter 23 and ultrasound catheter 25 are provided to be inserted throughout the procedure. EP catheter 19 performs sensing and stimulating functions. The ablation catheter 23 may represent an RF ablation catheter, a laser ablation catheter or a cryogenic ablation catheter. The ultrasound catheter 25 is configured to obtain ultrasound images of the region of interest, as well as images that indicate directly the position and placement of catheters and the ablation catheter relative to the region of interest. Surface ECG leads 27 are provided and attached to the patient to obtain surface ECG information. The surface ECG leads 27 and the catheters 19 are joined to a sensor amplifier 29 which amplifies signals sensed by the surface ECG leads 27 and EP catheters 19 prior to transmitting the sensed signals over a communications interface 24. When stimulus pulses are to be delivered to the patient, the stimulus signals are passed either around or through the sensor amplifier 29 to the corresponding catheters 19. An ablation source and controller 31 controls operation of the ablation catheter 23 and provides ablation-related data over the communications interface 24 to the workstation 10 (FIG. 1).

The beamformer 33 is responsible for transmit and receive beam forming operations. The link between the beamformer 33 and ultrasound catheter 25 may comprise individual channels associated with each transducer element within the transducer head of the ultrasound catheter 25. The beamformer 33 controls the phase and amplitude of each transmit signal delivered over the link to induce a transmit or firing operation by the ultrasound catheter 25. Reflected echoes are received at the ultrasound catheter 25 and delivered to the beamformer 33 as analog signals representative of the detected echo information at each individual transducer element. By way of example, the signals transmitted may represent low level analog RF signals transmitted to, or received from, the transducer elements of the ultrasound catheter 25. Optionally, the beamformer 33 may also control transmission and reception in connection with non-catheter type U/S probes, such as a transesophageal probe 47, a surface cardiac probe 49, an intravenous, intraarterial probes and the like.

The beamformer 33 includes a demodulator and filters to demodulate and filter the received analog RF signals and produce therefrom digital base-band I and Q data pairs formed from acquired data samples. The I, Q data pairs are derived from the reflected ultrasound signals from respective focal zones of the transmitted beams. The I and Q data pairs are filtered (e.g. such as in FIR filters that are programmed with filter co-effecients to pass a band of frequencies centered at a desired fundamental frequency of the transmit wave form or at harmonic or sub-harmonic frequencies of the transmit signal's fundamental frequency). The I, Q data pairs corresponds to each data samples within the region of interest. The beamformer 33 may pass the I, Q data pairs to a FIFO buffer 37 which then passes the I, Q data pairs over the communications interface 24 under the control of the controller 39. Alternatively, the beamformer 33 may directly stream the I, Q data pairs over the communications interface 24 as generated without buffering. Optionally, the beamformer 33 may store the I, Q data pairs in memory 7 in the ultrasound system 11. an ultrasound processor module 9 may be provided in the ultrasound system 11 to process the I, Q data pairs to form ultrasound images that are passed over communications interface 24 and/or stored in memory 7.

A real-time monitor 41, a review monitor 43 and documentation monitor 45 are located proximately the patient bed 13 for viewing by the procedure team and physician during the procedure monitors 41, 43 and 45 and are remotely controlled to present the same information as presented on the real-time monitor 48, operation monitor 50 and documentation monitor 52, respectively, located at the workstation 10.

The workstation 10 includes a signal management module 12 which is configured to receive and transmit a variety of signals and data that are conveyed to and from the patient over leads, cables, catheters and the like. Examples of signals that may be received by the signal management module 12 include intercardiac (IC) signals 14 from EP catheters, patient monitoring signals 15 (e.g., from a blood pressure cuff, SPO2 monitor, temperature monitor, C02 levels and the like), ECG signals 16 from surface ECG leads 27, pressure signals 18 from an open lumen catheter, and intracardiac signals. The signal management module 12 also receives fluoroscopic imaging data 20 from the fluoroscopic system 17, ultrasound imaging data 21 from the beamformer 33, and ablation data 22 (e.g., power, temperature, impedance) from the ablation source and controller 31. The fluoroscopic system 17 is an x-ray apparatus located in the procedure room. The ultrasound data 21 also may be collected at a transesphageal ultrasound probe, an intraoperative ultrasound probe, a transthoracic probe and/or a cardiac ultrasound probe.

Optionally, the ultrasound system 11 may be operated in an acoustic radiation force imaging (ARFI) mode. ARFI allows examination of the functionality of tissue subsets, such as in the heart, organs, tissue, vasculature and the like. ARFI is a phenomenon associated with the propagation of acoustic waves through a dissipative medium. It is caused by a transfer of momentum from the wave to the medium, arising either from absorption or reflection of the wave. This momentum transfer results in the application of a force in the direction of wave propagation. The magnitude of this force is dependent upon both the tissue properties and the acoustic beam parameters. The duration of the force application is determined by the temporal profile of the acoustic wave. ARFI images the response of tissue to acoustic radiation force for the purpose of characterizing the mechanical properties of the tissue. When the duration of the radiation force is short (less than 1 millisecond), the tissue mechanical impulse response can be observed. ARFI imaging has many potential clinical applications, including: detecting and characterizing a wide variety of soft tissue lesions, and identifying and characterizing atherosclerosis, plaque, and thromboses.

The communications interface 24 extends from the workstation 10 to the various equipment proximate the patient bed. When different rooms are provided the interface 24 extends through the wall or other divider separating the control and procedure rooms, into the procedure room. The communications interface 24 conveys, among other things, IC signals 14, patient monitoring signals 15, surface ECG signals 16, pressure signals 18, fluoroscopic imaging data 20, ultrasound imaging data 21 and ablation data 22. The content and nature of the information conveyed over the communications interface 24 is explained below in more detail. In one embodiment, the communications interface 24 is comprised of physical connections (e.g. analog lines, digital lines, coaxial cables, Ethernet data cables and the like or any combination thereof).

Optionally, the communications interface 24 may include, in whole or in part, a wireless link between the workstation 10 in the control room and one or more of the ultrasound, fluoroscopic, ablation, and EP instruments, devices, apparatus and systems in the procedure room 11. For example, ultrasound data 21 may be communicated wirelessly from a transmitter that is located within the procedure room 11 at the beamformer 33 to a receiver that communicates with the workstation 10 in the control room. The receiver would then convey the imaging data 21 to the signal management module 12.

The signal management module 12 selectively controls access of signals and data onto the communications interface 24. The signal management module 12 may comprise a simple configuration of switches that are manually operated by the user via the user interface 26. Alternatively, switches in the signal management module 12 may be automatically controlled by the processor 28 based upon various criteria including, among other things, the type of procedure currently being conducted. The signal management module 12 may include processing capabilities (e.g. a CPU, DSP and the like) to internally and automatically decide certain switching operations. The signal management module 12 may include memory, such as to temporarily buffer incoming and/or outgoing signals and/or data from/to the communications interface 24. The communications interface 24 conveys analog and digital signals. In the event that the communications interface 24 conveys analog signals, the signal management module 12 may include analog to digital converters to convert the analog signals to digital data and vise versa.

In one embodiment, the beamformer 33 may be located in the procedure room 11 proximate the patient and the ultrasound catheter 25. The beamformer 33 in the procedure room 11 converts the raw echo signals from the individual transducer element channels into I, Q data pairs, each data pair of which represents a data sample. The I, Q data pairs from the beamformer 33 are supplied as the ultrasound data 21 over the communications interface 24 to the workstation 10. The ultrasound data 21 is passed to the ultrasound processor unit 36. In the present example, the U/S processor module 9 is bypassed and not used. The ultrasound data processor module 36 may perform mid-processing operations (e.g., B-mode, Doppler, Strain, ARFI, etc.) upon the ultrasound I, Q data pairs.

In another embodiment, the U/S processor module 9 and the U/S system 11 is used for mid-processing operations and the U/S processing module 36 performs scan conversion operations. In yet another embodiment, the U/S processor modules 9 and 36 at the U/S system 11 and workstation 10, respectively, divide and share the mid-processing operations.

The signal management module 12 may communicate directly with an external stimulator 30. The stimulator 30 may deliver electrical signals (such as for pacing) directly over interface 24, or through the signal management module 12 and the IC leads 14, to one or more catheters 19 positioned within the patient. Examples of stimulators are the Micropace by Micropace Pty Ltd and the Bloom offered by Fisher Imaging.

The workstation 10 is used in an EP study to provide a detailed evaluation of the hearts electrical system. During an EP study, typically 3-5 catheters 19 are used. Each EP catheter 19 includes platinum electrodes spaced near the tip of the catheter, where such electrodes have the ability to record electrical signals from inside the heart as well as deliver stimulus pulses to the heart from different locations, such as to pace the heart. The workstation 10 evaluates normal and abnormal conductions and rhythms. The protocol used during the EP study may vary from site to site or procedure to procedure (e.g. corrected sinus node recovery time, AV Wenckebach and the like).

The stimulator 30 is utilized to induce a pacing train of pulses in order to stabilize a refractory period. The pacing train is considered to have "entrained" the heart once it has captured the heart for a predetermined series of beats. Once the heart is entrained, extra stimuli are added to mimic certain capabilities of the heart. The stimulator 30 may drive ventricular protocols through pacing from a ventricular catheter. One reason for ventricular pacing may be to assess the conduction retrograde through the AV node or bypass tract. When assessing conduction retrograde through the AV node, a VAWBK will also be obtained. Another ventricular protocol is the ventricular effective refractory period (VERPs). The stimulator 30 may also be used to induce arrhythmias. For example, during ventricular protocols, ventricular tachycardia or ventricular fibrillation may be induced as an end point. A patient's level of consciousness is assessed while attempts are made at overdrive pacing (if appropriate). When a patient loses consciousness, an external defibrillation shock is delivered.

The incoming signals from the patient over the communications interface 24 are passed from the signal management module 12 to a signal conditioning circuit 38 which performs various signal processing operations upon the incoming signals. The signal conditioning circuit 38 passes conditioned signals to the processor module 28 and optionally may pass the conditioned signals to a frame grabber 40 or directly to memory 42 or a database 44. The processor module 28 manages overall control and operation of the workstation 10. The processor module 28 receives user inputs through the user interface 26. The processor module 28 stores data, images and other information in the memory 42 and/or in the database 44. The frame grabber 40 also accesses memory 42 and database 44 in order to obtain and store various data, images and the like. While the memory 42 and database 44 are shown as part of the workstation 10, it is understood that one or both of the memory 42 and database 44 may be part of the workstation 10, separate from, but located locally to the workstation 10 (e.g. in the control room) or remote from the workstation 10 and the control room (e.g. in another part of the facility or at an entirely separate geographic location (e.g. a different hospital, university, state, country and the like)).

The memory 42 and database 44 may store diagnostic images, such as CT and MR images acquired prior to the procedure, and ultrasound images acquired prior to, during, or after the procedure. The stored images facilitate pre- and post-procedure analysis for image optimization, manipulation and analysis. The ultrasound images may represent intracardiac ultrasound images obtained from the ultrasound catheter 25. Optionally, the ultrasound images may be obtained utilizing a transesophageal probe 47, an interoperative probe, and an external cardiac probe 49.

In each of the workstation 10 and U/S system 11, the timing information may be derived from the time of day, or from a reference clock. Alternatively, the various processors may have synchronized clocks which result in all the various systems being synchronized to the identical spot in the cardiac cycle. Alternatively, the timing information may be associated with the cardiac cycle of the patient which is determined by the EP signals.

The processor module 28 communicates uni-directionally or bi-directionally with the display controller 46 which controls monitors 48, 50 and 52. The monitors 48, 50 and 52 may simply present displayed information as explained hereafter. Optionally, the monitors 48, 50 and 52 may include input buttons for operation by the user to directly enter certain commands and instructions at the monitor 48, 50 and 52. Optionally, the monitors 48, 50 and 52 may represent touch sensitive screens that enable the user to enter information directly by touching active areas of a corresponding monitor 48, 50 and 52.

In the example of FIG. 1, a touch sensor control 54 is illustrated that detects touch actions relative to monitor 48. The touch sensor control 54 provides the results of the touch action to the processor 28. The touch action result may simply represent an X,Y coordinate at which a touch event occurred. Alternatively, the touch sensor 54 may first determine the X,Y coordinate of the touch event and subsequently determine the intended action or instruction based upon the display content of monitor 48 under the control of the display controller 46. For example, the touch sensor control may return a "select drop down menu".

In the example of FIG. 1, monitors 48-52 have been assigned different categories of functions (e.g. real-time monitoring, operations monitoring, documentation monitoring and the like). Monitor 48 presents numerous windows, such as ablation window 56, a real-time EP monitoring window 58, a real-time image window 60 and a preprocessing planning window 62.

The monitor 50 displays windows related to operation control, such as an ICE user interface window 64, an EP/HD recording user interface window 66, a mapping user interface window 68 and a catheter steering user interface window 70. The user interface windows 64-70 allow the operator to enter and change parameters, modes, patient information, values and the like in connection with a particular EP study.

The monitor 52 is configured to present windows associated with documentation of a particular patient case. Monitor 52 presents a case review window 72, a case reporting window 74 and a case log window 76. The case-related windows 72-76 allow the user to review patient history information, as well as current patient information associated with the EP or HD study.

The workstation 10 integrates the display of ultrasound images with other EP or HD study information and/or ablation procedure information by utilizing one or more of monitors 48, 50 and 52. For example, real-time image window 60 may present ultrasound images obtained from an ultrasound catheter, while planning window 62 presents previously acquired CT or MR images. Integrating the ultrasound images into the workstation affords, among other things, an improved standard of care, increased user confidence and shorter procedure time.

Optionally, the real-time image window 60 may present ultrasound images as a cine loop, in which a sequence of ultrasound frames is acquired and associated with one or more cardiac cycles. The cine loop of ultrasound images may be repeatedly displayed or frozen. While the real-time image window 60 presents the ultrasound images, the real-time EP/HD window 58 simultaneously displays real-time EP signals corresponding to the ultrasound cine loop. The planning window 62 may present associated mapping data acquired earlier during the EP or HD study.

The signal management module 12 also communicates directly with an ablation control device 32 which is used to control various ablation procedures. The ablation control device 32 may constitute RF catheter ablation, laser catheter ablation, cryogenic ablation and the like. The ablation device 32 is attached to a generator 34 that produces the energy utilized to achieve ablation. For example, in an RF ablation or laser ablation system, the generator 34 represents a RF generator or a laser source. During RF catheter ablation, energy is delivered from a RF generator through an RF catheter having a tip located proximate anatomy that is desired to undergo ablation. Ablation is generally performed in order to locally destroy tissue deemed responsible for inducing an arrhythmia. The RF energy represents a low-voltage high-frequency form of electrical energy that produces small, homogeneous, lesions approximately 5-7 millimeters in diameter and 3-5 millimeters in depth.

The ablation device 32 may be used in a variety of procedures. The most common type of generic supra ventricular tachycardia (SVT) is atrioventricular nodule reentrant tachycardia (AVNRT). In the most common form AVNRT, the inferior atrianodule input to the atrioventricular (AV) node serves as the anterograde limb (e.g. the slow pathway) of the reentry circuit and the superior antrionodule input serves as the retrograde limb (e.g. the fast pathway). Typically, AVNRT is treated by targeting the slow pathway through ablation near the inferior tricuspid valve annulus at the level of the coronary sinus OS or somewhat higher. Another common type of SVT is orthodramic reciprocating tachycardia (ORT), a reentrant rhythm using the AV node as the anterograde limb and accessory AV connection (e.g. the accessory pathway) as the retrograde limb. The SVT rhythm disturbance can be cured by targeting the accessory pathway as it crosses the mitral or tricuspid valve annulus. Another type of SVT is unifocal atrial tachycardia which may arise in either atrium. The unifocal atrial tachycardia originating in the left atrium is treated through a transsceptal catherization through a foramen ovale or transceptal puncture.

Atrial flutter, another arrhythmia, is most commonly due to a large reentrant circuit in the right atrium, whereby entry proceeds counter clockwise up the atrial septum and down the lateral wall of the right atrium, inscribing inverted flutter waves in the inferior leads. The reentrant circuits associated with atrial flutter used an isthmus of tissue between the tricuspid valve annulus and the inferior vena cava. Linear ablation of the isthmus cures these common forms of atrial flutter. Atrial fibrillation is more commonly treated by crossing the intraarterial septum with a catheter and creating ablation lines in the left atrium which electrically isolates the pulmonary veins. The atrial fibrillation is generally curable and the patient does not require a pacemaker. Ablation may also be performed in connection with ventricular tachycardia.

RF catheter ablation is performed utilizing a sinusoidal high frequency (e.g. 500 kHz) form of electrical current that causes small lesions within the heart. Tissue destruction is primarily caused by thermal injury, such as desiccation necrosis. The RF energy causes resistive heating of a rim of tissue in direct contact with the electrode at the tip of the catheter. Tissue below the surface is heated by conduction of the heat from the para-electrode region. The lesion size is determined by the conduction of the heat through the tissue and by convective heat loss due to the blood pool. In general, the temperature at the interface between the electrode tip and the endocardial tissue should be approximately 50° Celsius or higher to cause tissue necrosis. Optionally, the tissue may be heated to higher temperatures. The size and depth of the lesion is controlled by the amount of energy delivered to the tissue. An acute lesion includes a central zone of coagulation necrosis surrounded by a border of hemorrhage and inflammation.

Figure 3:
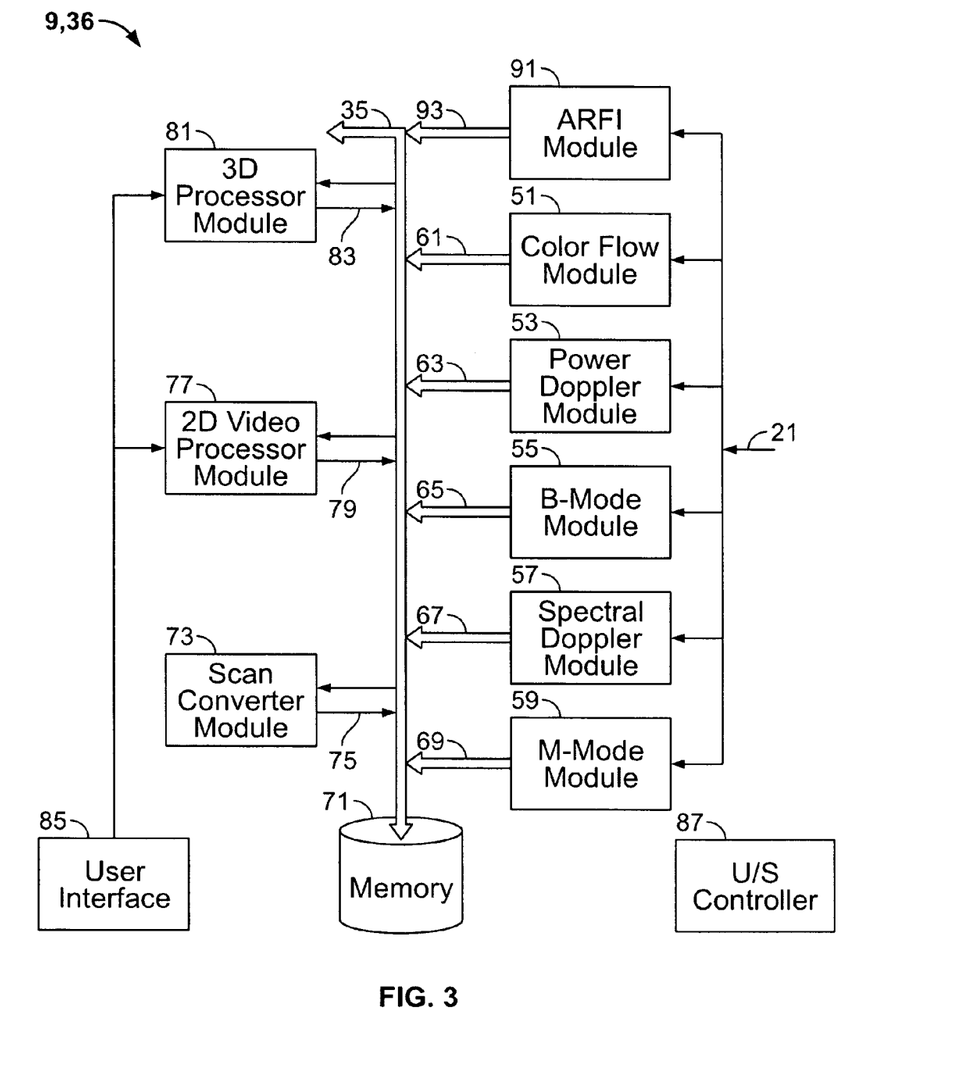
FIG. 3 illustrates a block diagram of the ultrasound processor unit of the workstation of FIG. 1 formed in accordance with an embodiment of the present invention.

FIG. 3 illustrates an exemplary block diagram of the ultrasound processor module 36 of FIG. 1 or the U/S processor module 9 of FIG. 2 formed in accordance with an embodiment of the present invention. The ultrasound processor module 9, 36 is illustrated conceptually as a collection of modules, but may be implemented utilizing any combination of dedicated hardware boards, DSPs and processors. Alternatively, the modules of FIG. 3 may be implemented utilizing an off-the-shelf PC with a single processor or multiple processors, with the functional operations distributed between the processors. As a further option, the modules of FIG. 3 may be implemented utilizing a hybrid configuration in which certain modular functions are performed utilizing dedicated hardware, while the remaining modular functions are performed utilizing an off-the shelf PC and the like.

The operations of the modules illustrated in FIG. 3 may be controlled by a local ultrasound controller 87 or by the processor module 28. The modules 51-59 perform mid-processor operations.

The ultrasound processor module 36 receives ultrasound data 21 in one of several forms depending upon the distribution of ultrasound operations between the ultrasound system 11 and workstation 10. In the embodiment of FIG. 3, the received ultrasound data 21 constitutes I, Q data pairs representing the real and imaginary components associated with each data sample. The I, Q data pairs are provided to a color-flow module 51, a power Doppler module 53, a B-mode module 55, a spectral Doppler module 57 and M-mode module 59. Optionally, other modules may be included such as a strain module, a strain rate module, ARFI module and the like. Each of modules 51-59 process the I, Q data pairs in a corresponding manner to generate color-flow data 61, power Doppler data 63, B-mode data 65, spectral Doppler data 67, M-mode data 69 and, ARFI module 91 all of which may be stored in memory 71 temporarily before subsequent processing and/or stored in memory 42 or database 42. The color-flow, power Doppler, B-mode, spectral Doppler and M-mode data 61-69 and ARFI data 93 are stored as sets of vector data values, where each set defines an individual ultrasound image frame. The vector data values are generally organized based on the polar coordinate system.

The scan converter module 73 reads from memory 71 the vector data values associated with an image frame and converts the set of vector data values to Cartesian coordinates to generate an ultrasound image frame 75 formatted for display. The ultrasound image frames 75 generated by scan converter module 73 may be passed back to memory 71 for subsequent processing or may be passed to the database 44 (FIG. 1), memory 42 and/or to the processor 28 or display controller 46.

Once the scan converter module 73 generates the ultrasound image frames 75 associated with B-mode data, color-flow data, power Doppler data and the like, the image frames may be restored in memory 71 or passed over bus 35 to the database 44, memory 42 and/or to the processor 28.

As an example, it may be desired to view a B-mode ultrasound image in real-time on the real-time image window 60 on monitor 48 associated with the ultrasound signals detected by an ultrasound catheter 25 (FIG. 2). To do so, the scan converter obtains B-mode vector data sets for images stored in memory 71. The B-mode vector data is interpolated where necessary and converted into the X,Y format for video display to produce ultrasound image frames. The scan converted ultrasound image frames are passed to the display controller 46 which may include a video processor that maps the video to a grey-scale mapping for video display. The grey-scale map may represent a transfer function of the raw image data to displayed grey levels. Once the video data is mapped to the grey-scale values, the display controller 46 controls the real-time monitor 48 to display the image frame in the real-time image window 60. The B-mode image displayed in the real-time image window 60 is produced from an image frame of data in which each datum indicates the intensity or brightness of a respective pixel in the display. The display image represents the tissue and/or blood flow in a plane through the region of interest being imaged.

The color-flow module 51 may be utilized to provide real-time two-dimensional images of blood velocity in the imaging plane. The frequency of sound waves reflected from the inside of the blood vessels, heart cavities, etc., is shifted in proportion to the velocity of the blood vessels; positively shifted for cells moving toward the transducer and negatively shifted for cells moving away from the transducer. The blood velocity is calculated by measuring the phase shift from firing to firing at a specific range gate. Mean blood velocity from multiple vector positions and multiple range gates along each vector are calculated and a two-dimensional image is made from this information. The color-flow module 51 receives the complex I, Q data pairs from the beamformer 33 (FIG. 2) and processes the I, Q data pairs to calculate the mean blood velocity, variance (representing blood turbulence) and total pre-normalized power for all sample volumes within the operator defined region.

The 2D video processor module 77 combines one or more of the frames generated from the different types of ultrasound information. For example, the 2D video processor modules 77 may combine a B-mode image frame and a color-flow image frame by mapping the B-mode data to a grey map and mapping the color-flow data to a color map for video display. In the final displayed image, the color pixel data is superimposed on the grey scale pixel data to form a single multi-mode image frame 79 that is again re-stored in memory 71 or passed over bus 35. Successive frames of color-flow and/or B-mode images may be stored as a cine loop in memory 71, memory 42 or database 44. The cine loop represents a first in, first out circular image buffer to capture image data that is displayed in real-time to the user. The user may freeze the cine loop by entering a freeze command at the user interface 85. The user interface represents a keyboard and mouse and all other commands associated with ultrasound system user interface.

The spectral Doppler module 57 operates upon the I, Q data pairs by integrating (summing) the data pairs over a specified time interval and then sampling the data pairs. The summing interval and the transmission burst length together define the length of the sample volume which is specified by the user at the user interface 85. The spectral Doppler module 57 may utilize a wall filter to reject any clutter in the signal which may correspond to stationery or very slow moving tissue. The filter output is then fed into a spectrum analyzer, which may implement a Fast Fourier Transform over a moving time window of samples. Each FFT power spectrum is compressed and then output by the spectral Doppler module 57 to memory 71. The 2D video processor module 77 then maps the compressed spectral Doppler data to grey scale values for display on the real-time monitor 48 as a single spectral line at a particular time point in the Doppler velocity (frequency) versus a time spectrogram.

A 3D processor module 81 is also controlled by user interface 85 and accesses memory 71 to obtain spatially consecutive groups of ultrasound image frames and to generate three dimensional image representation thereof, such as through volume rendering or surface rendering algorithms. The three dimensional images may be generated utilizing various imaging techniques, such as ray-casting, maximum intensity pixel projection and the like.

Figure 4:
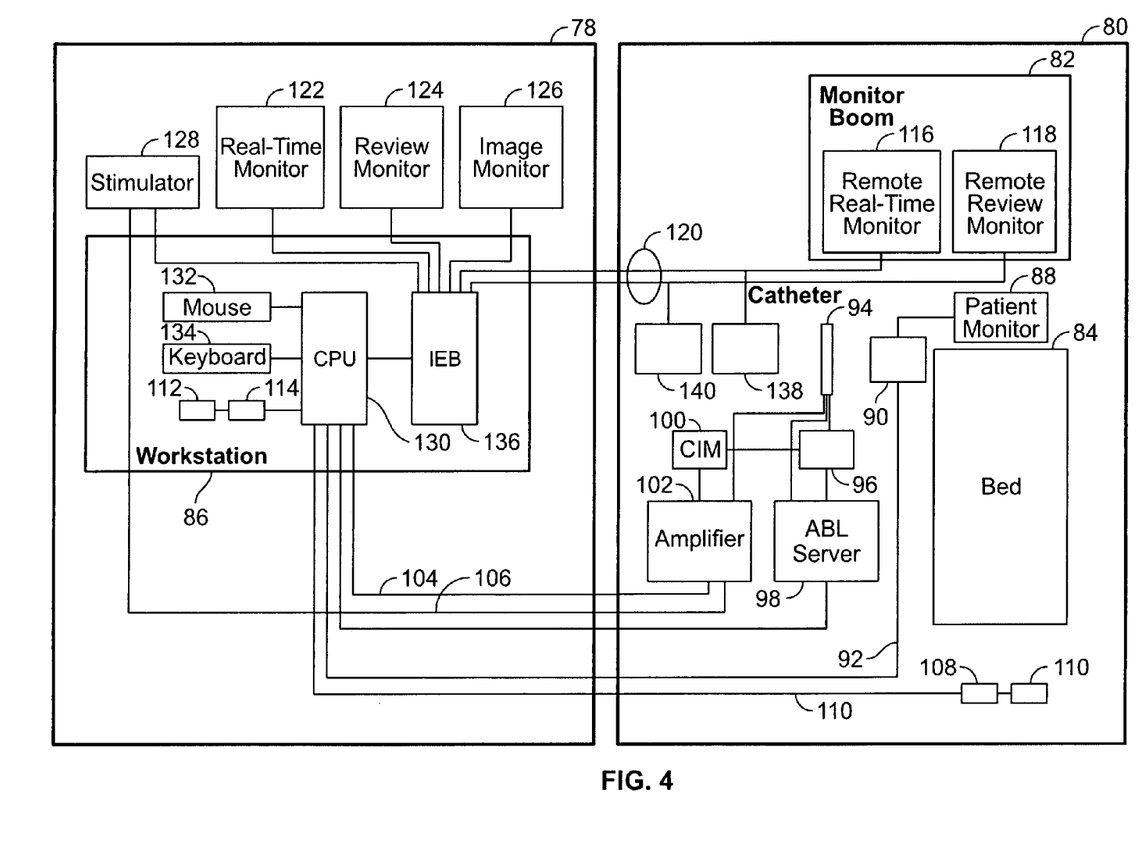
FIG. 4 illustrates a block diagram of an electrophysiology system distributed between multiple rooms within a physiology laboratory in accordance with an embodiment of the present invention.

FIG. 4 illustrates a block diagram of a system configuration for an alternative embodiment distributed between the areas associated with a physiology lab. The lab includes a control area 78 located immediately adjacent a procedure area 80 and a monitoring area 82. The control and procedure areas 78 and 80 may in separate rooms with a window provided between the rooms in order that the operator of a workstation 86 may view of the activities taking place in the procedure room.

The control area 78 includes the workstation 86 that it is joined to a real-time monitor 122, review monitor 124, image monitor 126 and stimulator 128. The workstation 86 includes a CPU 130 that is joined to a mouse 132 and keyboard 134 to facilitate user inputs. A display controller 136 is joined to the CPU 130 control the information and images presented on the monitors 116, 118, 122, 124 and 126. The display controller 136 is also joined directly to the stimulator 128 in order to obtain information associated with stimulus signals.

The procedure area 80 includes a patient bed 84. A patient monitor 88 is located proximate the patient to monitor the patient vital signs. An interface adapter 90 is joined with bedside peripheral devices. The interface adapter 90 enables information from the bedside peripheral devices to be received and processed by the patient monitor 88. The adapter 90 enables the peripheral device information to be displayed, trended and stored at the patient monitor 88. In addition, the interface adapter 90 provides the information, from the peripheral devices, to the workstation 86 over data link 92 which traverses the dividing wall between the procedure area 80 and control area 78. For example, a peripheral device may represent an endtidal CO2 module, that provides information used to guide conscious sedation of the patient.

A catheter 94 is attached to a catheter control module 96, which is joined with an ablation source 98 and a catheter imaging module 100. The catheter imaging module 100 is joined to an amplifier 102. Only one catheter 94 is shown, but multiple catheters 94 may be utilized. The catheters 94 may include one or more EP catheters, ICE catheters, ablation catheter and the like. The catheters 94 are attached to the catheter control module 96 simultaneously. For example, an EP catheter and an ablation catheter may be joined to the different input ports of the catheter control module 96.

The catheter control module 96 routes signals and data based upon the catheter source. For example, EP signals sensed at the catheter 94 are routed through the amplifier 102 over link 104 to the workstation 86. Stimulus signals from stimulator 128 are delivered, over link 106, through the amplifier 102, to the catheter 94. When catheter 94 represents an ablation catheter, the ablation source 98 delivers the necessary ablation energy (e.g., laser, RF, cryogenic) to the catheter 94. Signals and outputs are read from the ablation source 98 via an output from the ablation catheter designed for this purpose and a serial connection on the ablation device. Optionally, ablation energy may not be routed through the control module 96. When the catheter 94 represents an RF catheter, the ablation source 98 represents an RF signal generator. When the catheter 94 represents a cryogenic ablation catheter, the ablation source 98 supplies a cryogenic medium to the tip of the catheter 94 sufficient to cause tissue necrosis. Optionally, the ablation source 98 may be directly attached to an ablation catheter, thereby circumventing the catheter control module 96.

Speakers 108 and a microphone 110 are provided in the procedure area 80 and joined to the workstation 86 through link 109. The workstation 86 also includes speakers and a microphone 112 and 114 to enable the individuals in the procedure area 80 and in the control area 78 to communicate with one another.

The monitor area 82 includes one or more monitors, such as a real-time monitor 116 and a remote review monitor 118. The real-time and remote review monitors 116 and 118 are joined to the workstation 86 over links 120 present, to the people in the monitor area 82, the same information as illustrated on the real-time monitor 122 and review monitor 124 in the control area 78. An image monitor 126 is also provided in the control area 78, and may similarly be duplicated in the monitor area 82.

Optionally, the procedure area 80 may include one or more slave monitors, such as slave real-time monitor 138 and slave review monitor 140. The slave monitors 138 and 140 enable personnel in the procedure room to easily visualize the real-time IC signals, surface ECG signals, ultrasound images and the like.

Figure 5:
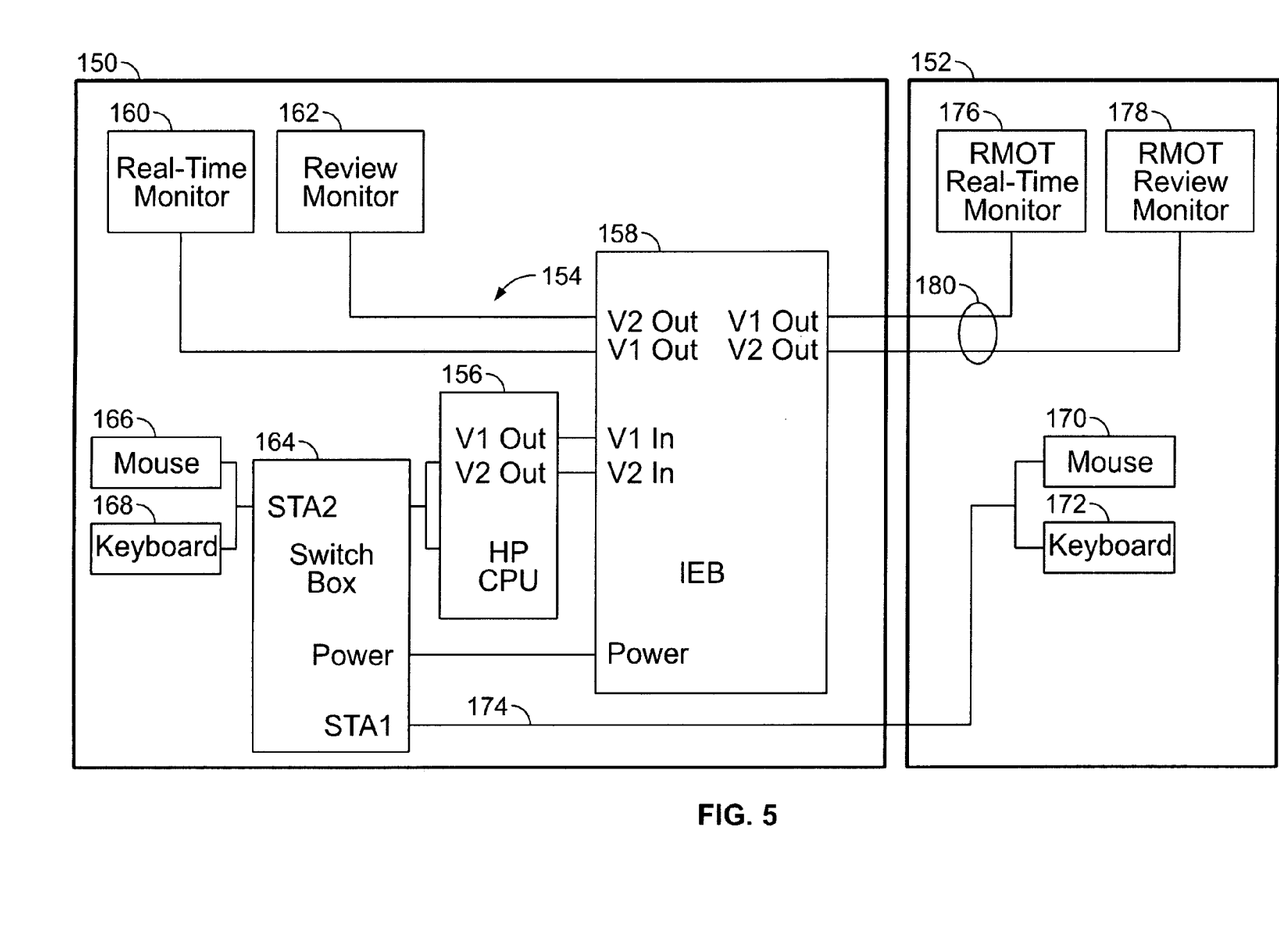
FIG. 5 illustrates a block diagram of an alternative physiology system distributed between multiple rooms within a laboratory in accordance with an embodiment of the present invention.

FIG. 5 illustrates an alternative embodiment configured to provide remote operator control. In FIG. 5, a control room 150 separated from a procedure room 152. The control room 150 includes a workstation 154 having a processor 156 that communicates with a display controller 158 to display information on real-time monitor 160 and review monitor 162. A switch box 164 interconnects a mouse and keyboard 166 and 168 with the CPU 156. The mouse and keyboard 166 and 168 are located at the workstation 154 in the control room 150 to facilitate user inputs and control. The switch box 164 is also joined, over a remote link 174, to a mouse and keyboard 170 and 172 which are provided in the procedure room 152. The mouse and keyboard 170 and 172 are located remote from the workstation 154 and a separate room, namely the procedure room 152. A remote real-time monitor 176 and a remote review monitor 178 are also provided in the procedure room 152 remote from the workstation 154. The remote real-time monitor 176 and review monitor 178 are controlled over remote links 180 by the display controller 158.

The remote mouse and keyboard 170 and 172 and the remote real-time and review monitors 176 and 178 allow a user to enter data directly into the workstation 154 through switch 164. The switch 164 automatically switches between the local and remote mouse and keyboard 166, 168 and 170, 172 such that only one combination of mouse and keyboard is active at any point in time.

Figure 6:
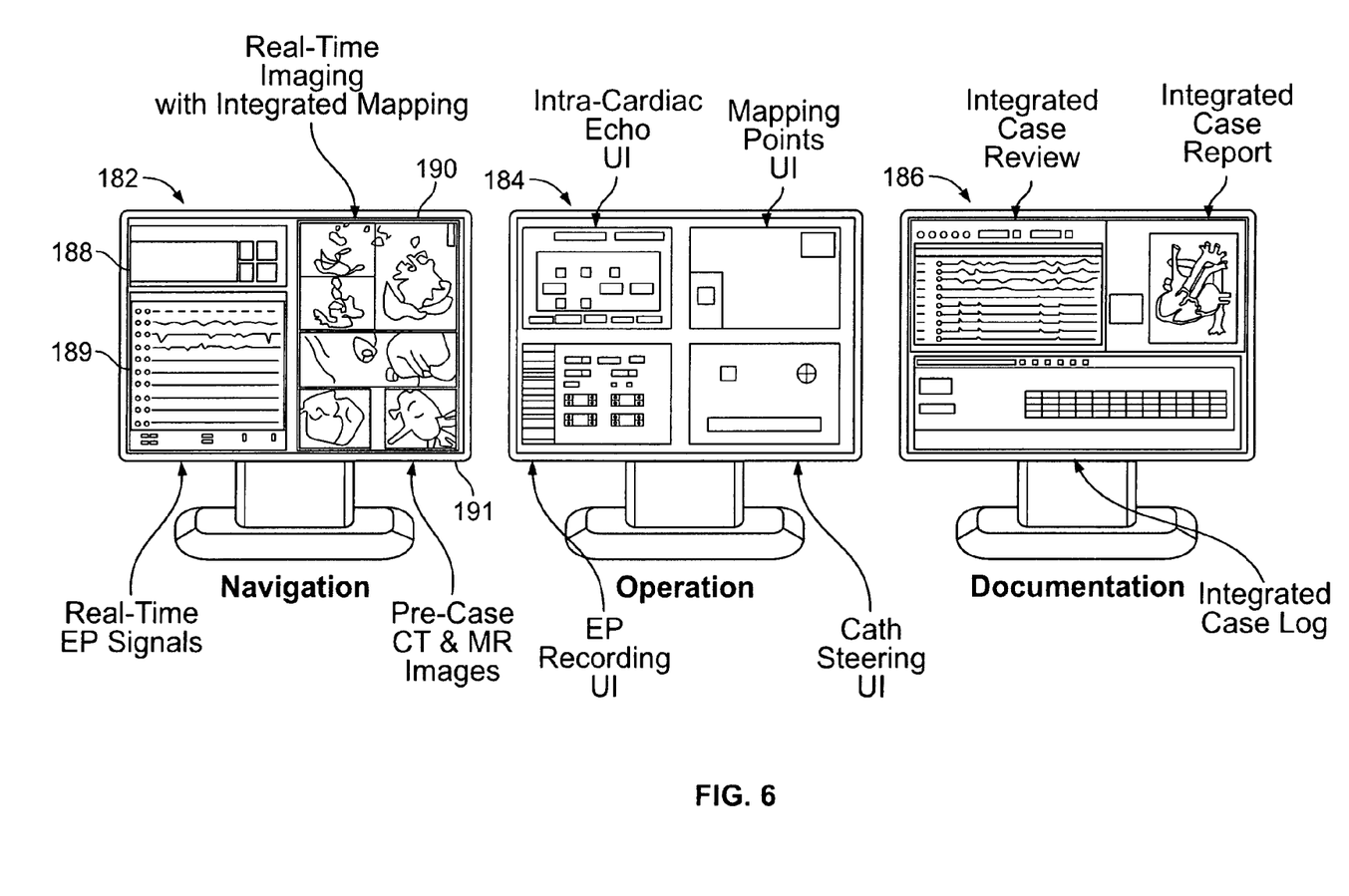
FIG. 6 illustrates exemplary window layout for a configuration of monitors for a physiology workstation formed in accordance with an embodiment of the present invention.

FIG. 6 illustrates more detailed examples of the window content that may be presented in various combinations on the monitors 48-52, 116-118, 118, 122-126, 160-162 and 176-178. The monitors in FIG. 6 represent a navigation monitor 182, an operations monitor 184 and a documentation monitor 186. The navigation monitor includes an ablation window 188, real-time EP signal window 189, real-time imaging window 190 with integrated mapping indicia and pre-case image window 191 (e.g. previously acquired CTR MR images). The operations monitor 184 includes windows associated with intracardiac echography, mapping, catheter steering and EP recording. The documentation monitor 186 includes windows associated with integrated case review, integrated case reports and an integrated case log.

Optionally, the beamformer 33 may be moved from the procedure room 11 and located at the ultrasound processor unit 36. In this embodiment, the ultrasound data 21 would represent raw echo signals conveyed over separate channels from each transducer element of an ultrasound device (e.g. probe or catheter). The raw echo signals from the transducer elements would not undergo beam-forming before arriving at the workstation 10. For example, the ultrasound catheters 19 may include a transducer having 64 elements and thus 64 separate channels may be organized within the ultrasound data 21. The raw echo ultrasound data 21 would then be routed to the ultrasound data unit 36 to perform beamforming processing to generate I, Q data pairs and from that generate ultrasound vector data sets, each set of which corresponds to a 2D image frame. The ultrasound vector data sets may include one or more of B-mode data, color flow data, power Doppler and the like. The ultrasound vector data sets may be stored directly in the database 44 and/or memory 42. The ultrasound vector data sets may be passed through signal conditioner 38 to processor 28.

Figure 7:
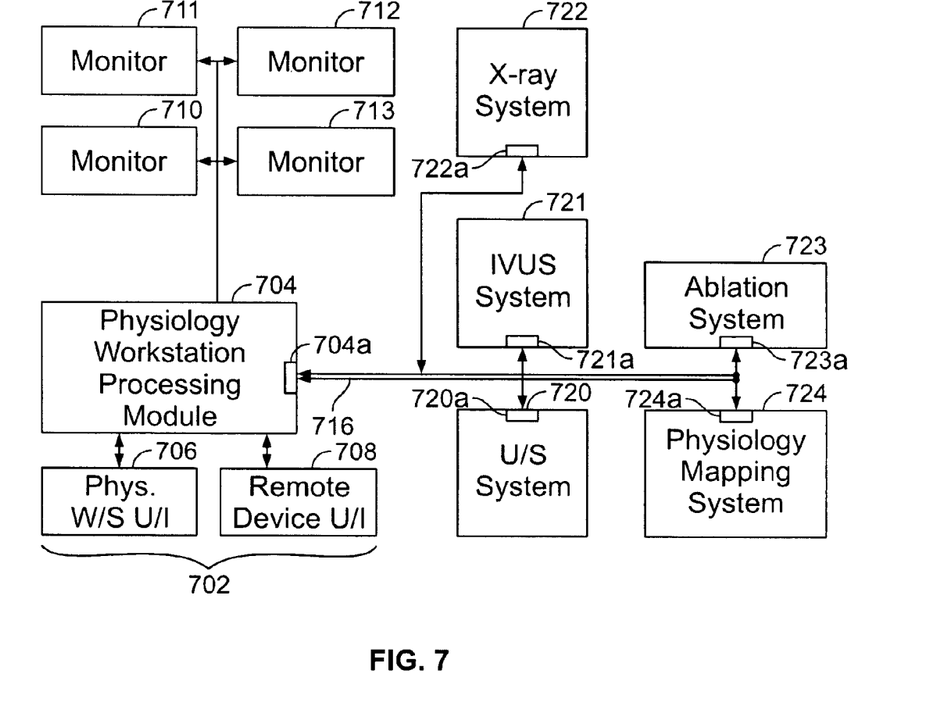
FIG. 7 illustrates a block diagram of an alternative embodiment in which remote control is provided for various systems and devices formed in accordance with an embodiment of the present invention.

FIG. 7 illustrates a block diagram of an alternative embodiment in which remote control is provided for various systems and devices. In FIG. 7, a physiology workstation 702 (e.g. EP or H. D. workstation) and includes a physiology workstation processing module 704 that communicates with, and is controlled by, a physiology workstation user interface 706. The physiology workstation 702 may be located in a new separate room (e.g. a control room) remote from the systems 720-724. Alternatively, the physiology workstation 702 may be located in the same room as the systems 720-724. A remote device user interface 708 also communicates with the physiology workstation processing module 704. The monitors 710-713 are joined to the physiology workstation processing module 704 to illustrate the various information, images, signals and the like explained above. A link 716 is maintained between the physiology workstation processing module 704 and various remote devices, such ultrasound system 720, IVUS system 721, x-ray system 722, ablation system 723 and physiology mapping system 724. The systems 720-724 may each include the associated types of acquisition apparatus (e.g. catheters, probes, C-arm, coils and the like, as well as monitors and user interfaces).

The link 716 may include one or more links connected to each of the systems 720-724. For example, the link 716 may include a single serial or parallel line directly extending from the remote device user interface 70821 of the systems 720-724, and attached thereto, at a user interface input. Alternatively or in addition, link 716 may include a data bus conveying serial or parallel data between the processors within module 704 and one or more of systems 720-724 (e.g. ECG data, EP data, HD data, image frames and the like). The link 716 may also include one or more video cables extending between a video output (e.g. VGA) at one of systems 720-724 and a video input at one or more of monitors 710-713.

Optionally, the link 716 may constitute a network connection, such as supporting an Internet protocol (IP) or the transmission control protocol (TCP), or other protocols. The data may be transmitted over link 716 as raw ultrasound or x-ray data, formatted in the Hypertext markup (HTML) language, and the like. Optionally, the link 716 may be constructed as a local area network configuration, a client/server configuration, an intranet configuration, a file sharing configuration and the like. Communications modules 704a and 720a-724a would be provided at each of the module 704 and systems 720-724 configured in accordance with the appropriate configuration. The communications modules 704a and 720a-724a may represent USB ports, while the link 716 represents a USB cable. Alternatively, the communications modules 704a and 720a-724a may represent serial or parallel connectors, HSSDC connectors, Fiber Channel connectors and the like, while the link 716 represents the corresponding type of communications medium. Alternatively, the link 716 may be wireless (e.g., RF, Bluetooth, etc.).

The remote device user interface 708 may be used to control the operation of one or more of the systems 720-724. For example, the remote device user interface seven OA may be used to enter system parameters, settings, modes and the like. The remote device user interface 708 permits the operator of the physiology workstation 702 to remotely control the operation, and remotely adjust the settings, modes and parameters, of one or more of the systems 720-724. The remote device user interface 708 improves workflow within the procedure room, increases productivity of an EP or HD team in the procedure room and end the review room, and decreases the overall procedure duration.

By way of example, when the remote device user interface 708 is used in connection with control of the ultrasound system 720 or IVUS system 721, the remote operator may be afforded the ability to change a modes, adjust the gain of the ultrasound probe or catheter, freeze select images on the monitor at the physiology workstation 702 and the monitor at the ultrasound system 720, and the like. Optionally, the remote device user interface 708 may constitute a dedicated keyboard identical to a keyboard provided with one of systems 720-724.

Figure 8:
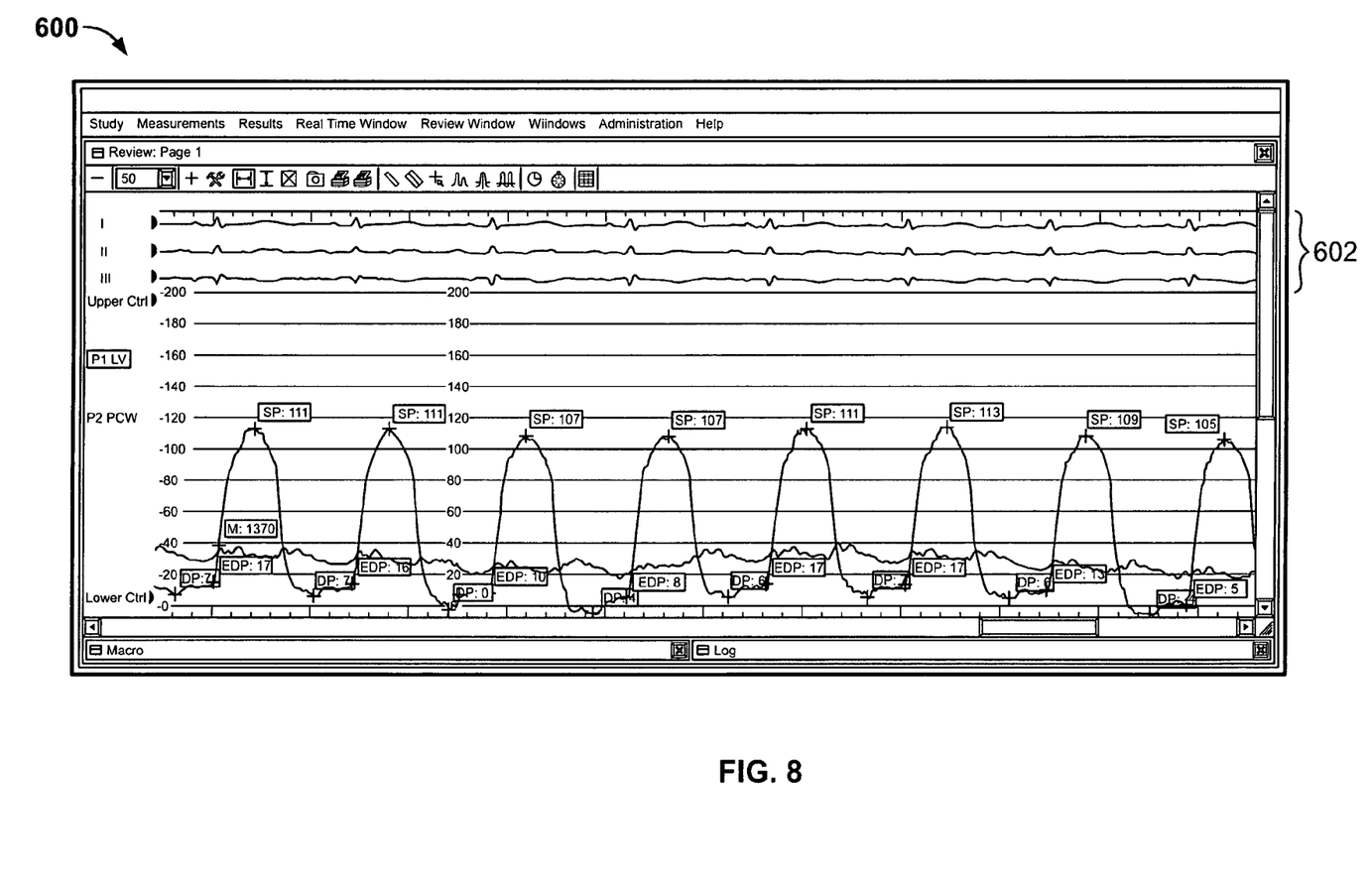
FIG. 8 illustrates a screenshot of an exemplary window presented on one of the monitors of the physiology workstation formed in accordance with an embodiment of the present invention.

FIG. 8 illustrates a screenshot of an exemplary window presented on one of the monitors of the physiology workstation. The screenshot of FIG. 8 represents a hemodynamic window 600, including three ECG traces, above a graph plotting the pressure at a particular point within the heart. In the example of FIG. 8, the pressure information is being obtained from an open lumen catheter having an outer end located proximate the mitral valve. The peaks and valleys within the graph represent the diastolic points (DP) and systolic points (SP) in the cardiac cycle. The pressure at each DP and SP is indicated as well. The EDP represents the end diastolic pressure. Along the bottom of the graph are a series of time stamps identifying the time (relative to the system clock) at which each pressure point was measured. The upper and lower controls (UpperCtrl and LowerCtrl) may be adjusted by the operator to adjust the dynamic range over which the pressure is measured.

While the invention has been described in terms of various specific embodiments, those skilled in the art will recognize that the invention can be practiced with modification within the spirit and scope of the claims.

What is claimed is:

1. A physiology workstation, comprising:
  a communications interface conveying intracardiac (IC) physiology signals derived from a region of interest of a subject and ultrasound data representative of the region of interest of the subject, the IC physiology signals being produced by at least one of an IC electrophysiology (EP) catheter and a hemodynamic (HD) catheter within a heart of a subject during at least one of an EP and HD procedure, the ultrasound data being obtained by an ultrasound device in real-time during the at least one of an EP and HD procedure carried out on the subject;
  a physiology processing unit receiving and processing the IC physiology signals during the at least one of an EP and HD procedure;
  an ultrasound processing unit receiving and processing the ultrasound data to generate ultrasound images, the physiology processing unit combining the IC physiology signals with the ultrasound images from the ultrasound processing unit; and
  a display unit displaying the IC physiology signals and the ultrasound images, the IC physiology signals and ultrasound signals being presented jointly to a user in real-time during the at least one of an EP and HD procedure being carried out on the subject.

2. The workstation of claim 1, wherein the display unit includes at least one monitor, the monitor co-displaying the IC physiology signals and ultrasound images in adjacent windows on a single display synchronized to a common spot in a cardiac cycle of the heart.

3. The workstation of claim 1, wherein the physiology processing unit, ultrasound processing unit and display unit are located in a control room that is divided and separate from a procedure room where the subject is located, the communications interface extending between the procedure and control rooms.

4. The workstation of claim 1, wherein the display unit includes at least one monitor that simultaneously displays IC physiology signals and real-time ultrasound images obtained in real-time, from the physiological processing unit, during the at least one of an EP and HD procedure, the at least one monitor simultaneously displaying images previously acquired from at least one of a MR, CT, PET, NM and X-ray system.

5. The workstation of claim 1, further comprising an ultrasound device having at least one of an intracardiac electrophysiology catheter, an handheld probe, an intraoperative probe, and a transesophageal probe.

6. The workstation of claim 5, further comprising a beamformer located proximate the ultrasound device and remote from the ultrasound processor unit, the beamformer operating upon raw echo signals received from the ultrasound device to form complex data pairs associated with data samples, the beamformer conveying the complex data pairs over the communications interface as the ultrasound data to the ultrasound processor unit.

7. The workstation of claim 5, further comprising a mid-processor located proximate the ultrasound device and remote from the ultrasound processor unit, the mid-processor operating upon ultrasound signals received from the ultrasound device to form vector data values associated with ultrasound images, the mid-processor processing the ultrasound signals based on at least one of color flow, power Doppler, B-mode, spectral Doppler, and M-Mode operations to form the vector data values, the mid-processor conveying the vector data values over the communications interface to the ultrasound processor unit.

8. The workstation of claim 5, further comprising a scan converter module located proximate the ultrasound processor unit and remote from the ultrasound device, the scan converter module operating upon ultrasound signals received from the ultrasound processor unit to form ultrasound images, the ultrasound images including at least one of color How, power Doppler, B-mode, spectral Doppler, ARFI and M-Mode information, the scan converter module conveying the ultrasound images over the communications interface to the ultrasound processor unit.

9. The workstation of claim 5, wherein the ultrasound processor unit comprises a beamformer, located remote from the ultrasound device, that receives raw echo signals as the ultrasound data over the communications interface from the ultrasound device, the beamformer performing beamforming operations upon the raw echo signals.

10. The workstation of claim 5, wherein the ultrasound processor unit comprises a mid-processor, located remote from ultrasound device, that receives complex data pairs as the ultrasound data over the communications interface, the mid-processor operating upon the data pairs to form vector data values associated with ultrasound images, the mid-processor processing the data pairs based on at least one of color flow, power Doppler, B-mode, spectral Doppler, ARFI and M-Mode operations to form the vector data values.

11. The workstation of claim 5, wherein the ultrasound processor unit comprises a scan converter module, located remote from ultrasound device, that receives vector data values as the ultrasound data over the communications interface, the scan converter module operating upon the vector data values to form ultrasound images, the ultrasound images including at least one of color flow, power Doppler, B-mode, spectral Doppler, ARFI and M-Mode information.

12. The workstation of claim 5, wherein the physiology and ultrasound processing units represent sets of functional electrophysiology and ultrasound operations, respectively, performed in a time shared manner by at least one common CPU, the at least one common CPU being located in a control room separate from a procedure room in which the ultrasound device is utilized with the subject.

13. The workstation of claim 1, wherein the ultrasound and physiology processing units are located in a common housing of the workstation in a control room that is remote from a procedure room in which the subject is located.

14. The workstation of claim 1, wherein the ultrasound and physiology processing units are located in a control room that is remote from a procedure room in which the subject is located.

15. The workstation of claim 1, wherein the display unit further comprises monitors located in a control room and external display links to drive remote slave monitors located in at least one of a procedure room and a remote monitoring room that are separate from the control room.

16. The workstation of claim 1, further comprising a fluoroscopy unit for obtaining fluoroscopic images of the region of interest, the physiology processing unit correlating the ultrasound images and the fluoroscopy images, both obtained in real-time during a procedure, based on the IC physiology signals.

17. The workstation of claim 16, further comprising memory storing fluoroscopy and ultrasound images each having a time stamp identifying when the fluoroscopy and ultrasound images were obtained with respect to a cardiac cycle, the physiology processing unit generating the time stamps based on the IC physiology signals.

18. The workstation of claim 1, further comprising memory storing non-ultrasound and ultrasound images each having a time stamp identifying when the non-ultrasound and ultrasound images were obtained with respect to one of a system clock and a cardiac cycle, the physiology processing unit generating the time stamps.

19. The workstation of claim 1, further comprising a frame grabber time stamping individual frames of ultrasound images based on a system clock.

20. The workstation of claim 1, further comprising a user interface for selecting a time log from the IC physiology signals, the physiology processing unit controlling the display unit to display an ultrasound image obtained at a point in time corresponding to the time log selected from the IC physiology signal.

21. The workstation of claim 1, wherein the display unit displays a cine loop of frames of the ultrasound images, obtained from the physiological processing unit, while simultaneously advancing marker indicia across the IC physiology signals displayed, the marker indicia correlating each of the frames of the ultrasound images with a point on the IC physiology signals at which the corresponding frame of the ultrasound images was obtained.

22. The workstation of claim 1, wherein the display unit includes a main monitor located in a procedure room proximate the subject and includes a slave monitor in a control room separate from the procedure room, the main and slave ultrasound monitors presenting the ultrasound images in real-time during a procedure performed on the subject.

23. The workstation of claim 1, further comprising an ultrasound device configured to transmit and receive ultrasound energy to and from a region of interest of the subject, the ultrasound device generating the ultrasound data based on received ultrasound energy.

24. The workstation of claim 1, wherein the display unit comprises a documentation monitor that includes windows associated with case review, case reports, and a case log for the at least one of an EP and HD procedure.

25. The workstation of claim 1, wherein the display unit comprises a real-time IC physiology signal window for presenting at least one of EP and HD physiology signals, and a real-time ultrasound image window, the real-time ultrasound window including mapping indicia representing positions on the ultrasound image at which the at least one of EP and HD physiology signals were obtained.

26. The workstation of claim 1, wherein the display unit comprises a user interface window allowing an operation to enter and change parameters in connection with the at least one of an EP and HD procedure.

27. The workstation of claim 1, further comprising:
a patient monitor located proximate the subject to monitor the subject's vital signs; and an adapter configured to be joined to peripheral devices coupled to the subject, the adapter providing information from the peripheral devices to the patient monitor and over the communications interface to the physiology processing unit.

28. An integrated physiology workstation, comprising:

a workstation housing;

a signal management module, provided in the workstation housing, configured to receive at least one of intracardiac (IC) electrophysiology (EP) signals and IC hemodynamic (HD) signals from at least one of an EP catheter and HD catheter within a heart of a subject during at least one of an EP and HD procedure, the signal management module configured to communicate with, and receive stimulus pulses, from a stimulator, and direct the stimulus pulses to the at least one of an EP and HD catheter within the heart;

an ultrasound processing unit, provided in the workstation housing, configured to receive and process ultrasound data obtained by an ultrasound device in real-time during the at least one of an EP and HD procedure;

a physiology processing unit coupled to the signal management module and provided in the workstation housing, configured to receive and process the at least one of IC EP and HD signals in real-time during the at least one of an EP and HD procedure; and a display unit displaying the IC EP and HD signals and the ultrasound images, the IC EP and HD signals and ultrasound signals being presented jointly to a user in real-time during the at least one of an EP and HD procedure being carried out on the subject.

29. The workstation of claim 28, wherein the physiology processing unit manages control and operation of the workstation and the ultrasound processing unit in connection with the at least one of an EP and HD procedure.

30. The workstation of claim 28, further comprising memory coupled over at least one bus to the physiology and ultrasound processing modules to store the ultrasound images and the at least one of IC EP and HD signals.

* * * * *